United States Patent
Khoja et al.

(10) Patent No.: US 11,215,622 B2
(45) Date of Patent: Jan. 4, 2022

(54) GENERATION OF CFDNA REFERENCE MATERIAL

(71) Applicant: Covaris, Inc., Woburn, MA (US)

(72) Inventors: Hamid Khoja, Rancho Santa Margarita, CA (US); James A. Laugharn, Jr., Boston, MA (US); Hans-Ulrich Thomann, Stow, MA (US)

(73) Assignee: Covaris, Inc., Woburn, MA (US)

( * ) Notice: Subject to any disclaimer, the term of this patent is extended or adjusted under 35 U.S.C. 154(b) by 0 days.

(21) Appl. No.: 15/877,422

(22) Filed: Jan. 23, 2018

(65) Prior Publication Data

US 2018/0217161 A1 Aug. 2, 2018

Related U.S. Application Data

(60) Provisional application No. 62/451,319, filed on Jan. 27, 2017.

(51) Int. Cl.
| | |
|---|---|
| *G01N 33/68* | (2006.01) |
| *G01N 33/574* | (2006.01) |
| *G01N 33/53* | (2006.01) |
| *C12Q 1/6806* | (2018.01) |

(52) U.S. Cl.
CPC ....... *G01N 33/6875* (2013.01); *C12Q 1/6806* (2013.01); *G01N 33/5308* (2013.01); *G01N 33/57496* (2013.01); *G01N 2570/00* (2013.01)

(58) Field of Classification Search
CPC ......... G01N 33/6875; G01N 33/57496; C12Q 1/6876
See application file for complete search history.

(56) References Cited

U.S. PATENT DOCUMENTS

| | | | | |
|---|---|---|---|---|
| 6,046,165 A | * | 4/2000 | Laughon ............ | C07K 14/4703 514/44 R |
| 9,499,870 B2 | | 11/2016 | Babiarz et al. | |
| 2002/0076711 A1 | * | 6/2002 | Wolffe ............... | C07K 14/4702 435/6.12 |
| 2007/0141584 A1 | * | 6/2007 | Roberts ............... | C12Q 1/6837 435/6.12 |
| 2009/0191563 A1 | * | 7/2009 | Steemers ............ | C12Q 1/6806 435/6.11 |
| 2015/0161982 A1 | * | 6/2015 | Laugharn, Jr. ........... | B01J 19/10 367/138 |
| 2016/0097088 A1 | * | 4/2016 | Zheng ................. | C12Q 1/6806 506/2 |

FOREIGN PATENT DOCUMENTS

WO WO 2015/048535 A1 4/2015

OTHER PUBLICATIONS

Khoja et al, Chromatin Shearing Based on Covaris Adaptive Focused Acoustics (AFA), 2009, poster presentation, p. 1 (Year: 2009).*
Khoja et al, Chromatin Shearing Based on Covaris Adaptive Focused Acoustics (AFA), 2009, poster presentation, p. 1, publication date support document, p. 1 (Year: 2009).*
Khoja et al poster presentation at 6th Annual sequencing, finishing, Analysis in the future meeting, Santa Fe, New Mexico, Jun. 1 to Jun. 13, 2011. poster FF 0077 (Year: 2011).*
Brouchovsky et al, Partial Purification of Nuclear Androgen Receptor by Micrococcal Nuelease Digestion of Chromatin and Hydrophobic Interaction Chromatography, 1981, Eur. J. Biochem. 120, 399-405. (Year: 1981).*
Leuba et al, On the location of linker DNA in the chromatin fiber, Studies with immobilized and soluble micrococcal nuclease, 1994, J. Mol. Biol., 235, 871-880. (Year: 1994).*
Kensche et al, The nucleosome landscape of Plasmodium falciparum reveals chromatin architecture and dynamics of regulatory sequences, 2016, Nucleic Acids Research, 44, 2110-2124 (Year: 2016).*
Kensche et al, The nucleosome landscape of Plasmodium falciparum reveals chromatin architecture and dynamics of regulatory sequences, 2016, Nucleic Acids Research, 44, supplemental information, pp. 1-21 (Year: 2016).*
Kensche et al, The nucleosome landscape of Plasmodium falciparum reveals chromatin architecture and dynamics of regulatory sequences, 2016, Nucleic Acids Research, 44, supplemental figures, pp. 1-9 (Year: 2016).*
Lo et al, Maternal Plasma DNA Sequencing Reveals the Genome-Wide Genetic and Mutational Profile of the Fetus, 2010, Sci Transl Med 2, 61ra9161ra91, pp. 1-15. (Year: 2010).*
Snyder et al, Cell-free DNA Comprises an In Vivo Nucleosome, Footprint that Informs Its Tissues-Of-Origin, 2016, cell, 164, 57-68 (Year: 2016).*
Holdenrieder, Cell-Free DNA in Serum and Plasma: Comparison of ELISA and Quantitative PCR, 2005, Clinical Chemistry, 51, 1544-1546. (Year: 2005).*

* cited by examiner

*Primary Examiner* — Narayan K Bhat
(74) *Attorney, Agent, or Firm* — Wolf, Greenfield & Sacks, P.C.

(57) ABSTRACT cfDNA reference material, for example, for use in verifying the accuracy and effectiveness of a diagnostic test, is generated from chromatin which may be sourced from whole cells. The chromatin may be treated with formaldehyde to form crosslinks between DNA and histones, for example, while the chromatin is contained within nuclear and/or plasma membranes. The fixed chromatin may be sheared by acoustic energy, which may also be used to lyse cell membranes within which the fixed chromatin may be contained. The sheared chromatin may be treated with an enzyme, such as micrococcal nuclease, to digest chromatin in linker regions of the DNA between nucleosomes and generate nucleosome material for use as cfDNA reference material.

20 Claims, 3 Drawing Sheets

GENERATION OF CFDNA REFERENCE MATERIAL

RELATED APPLICATIONS

This Application claims priority under 35 U.S.C. § 119(e) to U.S. Provisional Application Ser. No. 62/451,319, entitled "GENERATION OF CFDNA REFERENCE MATERIAL" filed on Jan. 27, 2017, which is herein incorporated by reference in its entirety.

BACKGROUND

1. Field of the Invention

Systems and methods for creating cell-free DNA (cfDNA) reference materials are generally disclosed.

2. Related Art

Detection and/or quantitation of certain biomarkers such as cell free DNA (cfDNA) in biological samples like blood, saliva, sputum, stool, urine, cerebral spinal fluid, or tissue can help to diagnose disease, establish a prognosis, and/or aid in selecting or monitoring treatment. For example, the concentration of certain genetic markers in cfDNA can indicate cancer progression or treatment success, and can have utility in noninvasive prenatal testing (NIPT) for the detection of trisomy or monosomy, as well as short insertion and deletion mutations in an unborn child (J. Clin. Med. 2014, 3, 537-565; doi:10.3390/jcm3020537). Also, relative concentrations (or profiles) of specific metabolites or RNAs in venous blood samples can indicate increased risk of conditions such as insulin resistance or obstructive coronary artery disease (Cobb et al. (2013) A Novel Fasting Blood Test for Insulin Resistance and Prediabetes. J Diabetes Sci Technol 2013; 7(1):100-110; Rosenberg et al (2010) Multi-center Validation of the Diagnostic Accuracy of a Blood-Based Gene Expression Test for Assessing Obstructive Coronary Artery Disease in Nondiabetic Patients. Ann Intern Med. 2010; 153(7):425-434). Specific changes in the sequence or modifications of certain DNAs present in stool samples can indicate the presence of colon cancer (Imperiale et al (2014) Multitarget Stool DNA Testing for Colorectal-Cancer Screening. N Engl J Med 2014; 370:1287-1297), and the presence of viral proteins or RNAs in dried blood spots can allow diagnosis of infectious diseases such as AIDS.

SUMMARY OF INVENTION

Since cfDNA can be used effectively in detecting, diagnosing and/or treating disease, a variety of different diagnostic tests have been developed to detect and monitor cfDNA in blood and other samples. As described in U.S. Pat. No. 9,499,870, for example, such diagnostic tests must be verified for accuracy in detecting cfDNA, e.g., to be authorized for use by regulatory agencies, insurance carriers or other entities. There is thus a need for synthetic cfDNA reference material, i.e., material that can be reproducibly made, has known properties and suitably mimics naturally occurring cfDNA for purposes of verifying that a particular diagnostic test or other protocol is effective and accurate.

In one aspect of the invention, a method for generating cfDNA reference material includes providing chromatin including DNA wrapped around corresponding histones to form nucleosomes. The chromatin may be provided outside of any cellular membrane, or contained within a nuclear membrane and/or plasma membrane. For example, chromatin may be provided in whole cells with intact plasma and nuclear membranes, or may be provided within a nuclear membrane only. The chromatin may be provided in a variety of ways and/or from different sources, e.g., from blood drawn from a subject, from an engineered or other cell line such as the GM24385 cell line available from Coriell Institute for Medical Research, from one or more tissue samples, etc. In some embodiments, it may be useful to have the DNA of the chromatin or cells sequenced or otherwise defined so that synthetic cfDNA created can have known properties. That is, synthetic cfDNA reference material created from known starting materials can be expected to behave or interact with diagnostic tools in a predictable way, increasing the value of the synthetic cfDNA reference material. If chromatin is provided within a cell, cell membranes may be lysed using any suitable technique to release chromatin for subsequent processing, or the chromatin may remain within one or more cell membranes for subsequent processing.

With a suitable set of chromatin provided, the chromatin may be treated with formaldehyde to generate crosslinks between DNA and histones. (See for example Hoffman et al (2015) Formaldehyde Crosslinking: a Tool for the Study of Chromatin Complexes. J Biol Med. 2015; 290(44):26404-26411). Such treatment may occur at any suitable time, such as with chromatin located within a cell (cells may be treated with formaldehyde at the time of harvesting or otherwise taking a sample that includes the whole cells, e.g., when blood is drawn), or after chromatin is released from a corresponding cell. One possibility is to lyse the cell membranes to release the nuclei, which are subsequently separated from other cell portions and then treated with formaldehyde to fix the chromatin. The formation of crosslinks helps to stabilize chromatin by covalently crosslinking histones, transcription factors, and any protein complexes that are associated with the chromatin to the corresponding DNA. Crosslinks of DNA to the histone complex maintains a tight bond between DNA and a corresponding histone octamer around which the DNA is wrapped. While crosslinks may be formed between DNA and the histone around which it is wrapped, crosslinks of DNA segments that are not in close contact to histones, such as linker segments between nucleosomes, may be crosslinked to a much lesser degree or not at all. For example, in some cases, a 147 bp segment of DNA may be wrapped around a corresponding histone octamer 1.75 times to form a single nucleosome. DNA in these wrapped segments may be crosslinked to the corresponding histone. However, linker DNA segments (e.g., having a length of 20-80 bp) that link one nucleosome to another may not have crosslinks formed with any histone. These linker segments lacking crosslinks may be more readily sheared and/or enzymatically digested to form single nucleosomes, and thus improve the quality of synthetic cfDNA produced because the resulting nucleosome material will more closely mimic the characteristics of natural cfDNA. (It is unlikely that enzymes, for example nucleases, will be able to hydrolyze DNA segments that are crosslinked to histone complex, since there is steric hindrance.)

The chromatin having crosslinks formed by formaldehyde treatment may subsequently be exposed to acoustic energy to shear the chromatin. For example, focused acoustic energy may be used to shear the chromatin into fragments having a size of 1-5 kbp. If the formaldehyde-treated chromatin is provided within a cell membrane, the acoustic energy may also be used to lyse cell membranes to release the chromatin, e.g., cause the chromatin to be released from nucleic and cell membranes by adjusting a porosity of the membranes or physically opening the membranes to allow the DNA to escape. Alternately, cell membranes may be lysed using other techniques, such as a lysing buffer, to release the fixed chromatin, if needed. As noted above, chromatin may be treated with formaldehyde while contained within a matrix surrounded by a cell membrane (plasma or nuclear membrane), or after being released from any such matrix by porating the membrane with acoustic energy, lysis reagents, or the like. Thus, formaldehyde-treated cell membranes may be lysed if needed to release chromatin, or the fixed chromatin may be sheared without any need to lyse cell membranes where no such membranes are present.

The sheared chromatin can be used to generate cfDNA reference material, but in at least some cases, the sheared chromatin must be reduced to smaller fragments sizes because the nucleosomal fraction of native cfDNA consists of a population of relatively smaller fragment sizes of around 160-200 kbp. As noted above, focused acoustic energy may be used to shear the formaldehyde crosslinked chromatin into smaller fragments in the size range of 1-5 kb, but these fragment sizes may be too large to mimic native cfDNA. To form smaller chromatin fragments, the sheared chromatin may be treated with an enzyme to digest DNA in linker regions of the chromatin between nucleosomes and generate nucleosome material that can be used as synthetic cfDNA reference material. Micrococcal nuclease (MNase) may be used to generate such nucleosomes, e.g., with an average fragment size of around 147-195 bp. A mix of endo- and exo-nucleases, a mix of different exonucleases or a mix of different endonucleases may also be used. Endonuclease examples are type I, II, III, IIG, IIP, IIS, IV endonucleases (such as restriction nucleases), Flap Endonuclease, Endonuclease II, Mung Bean nuclease I, S1 Nuclease, *Neurospora crassa* endonuclease, Dnase I, AP endonuclease, Endo R. Exonuclease examples are prokaryotic Micrococcal exonuclease, Exonuclease I, Exonuclease III, Exonuclease IV, Exonuclease V, Exonuclease VIII, human or yeast Exonuclease I, or Mung Bean Exonuclease.

In some embodiments, the cell membranes may be lysed and/or shearing of chromatin may be performed by focused acoustic energy while the cells are located in a buffer solution that is compatible with enzyme treatment, such as use of MNase or other exonucleases, or endonucleases, or cocktails thereof, to digest portions of the DNA. Thus, the chromatin need not be removed from a solution used to lyse the cells and/or shear the chromatin prior to enzyme treatment. Instead, nuclease may be added directly to the lysing or shearing buffer and the DNA and enzymatic digestion completed without having the separate the chromatin from the lysing or shearing buffer. This may significantly help increase yield of desired nucleosome material and simplify the production of synthetic cfDNA reference material.

The nucleosome material generated after enzymatic digestion may be used as a cfDNA reference material alone, or in combination with other DNA fragments or other material, such as DNA fragments that are not contained in the nucleosomal fraction but are present in the heterochromatineal fraction of the nucleus. Such DNA is accessible for gene-expression and may contain important genetic information that is not present in the nucleosomal fraction. For example, the nucleosome material generated by enzyme treatment may be combined with other DNA fragments, e.g., to provide the combined nucleosome material and DNA fragments with an average fragment size of 165 to 180 bp as well as DNA fragments of 1 kb and greater. In other embodiments, the nucleosome material may be combined with DNA fragments having known mutations to create a cfDNA reference material with a desired mutation frequency. By combining the nucleosome material with DNA fragments having known mutations, the cfDNA material may allow for verification that particular cfDNA material having those specific mutations can be detected or otherwise identified by a diagnostic or other test.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Aspects of the invention are not limited in application to the details of construction and the arrangement of components set forth in the following description or illustrated in the drawings. Other embodiments may be employed and aspects of the inventions may be practiced or be carried out in various ways. Also, the phraseology and terminology used herein is for the purpose of description and should not be regarded as limiting.

Figure 1:
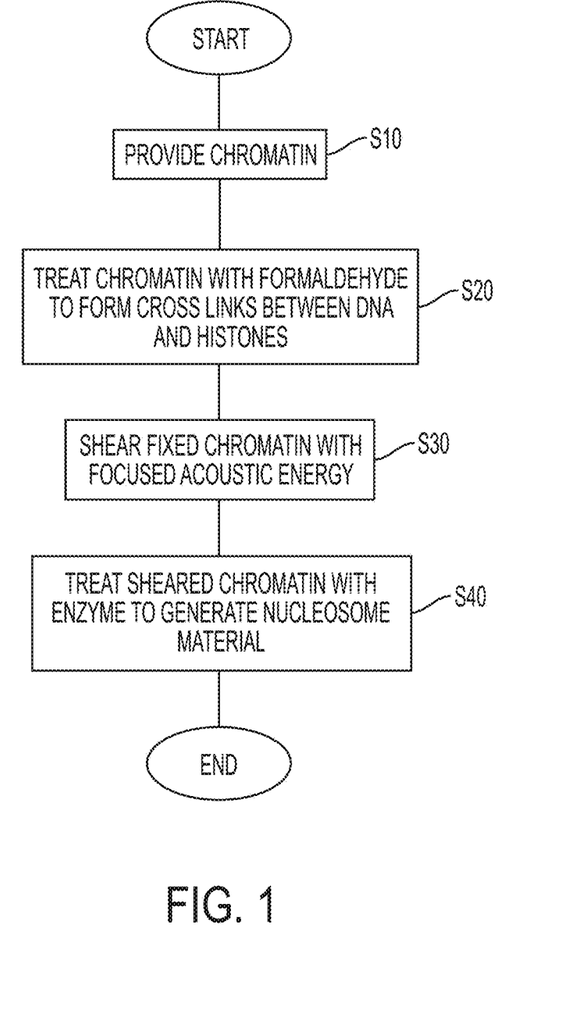
FIG. 1 shows steps in a method for forming a cfDNA reference material in an illustrative embodiment.

FIG. 1 shows steps in an illustrative method for forming synthetic cfDNA reference material. While examples are provided to illustrate embodiments in accordance with aspects of the invention, such aspects should not be construed as limited to these embodiments. In step S10, chromatin having DNA wrapped around corresponding histones to form nucleosomes is provided. This configuration of chromatin is typically found in eukaryotic cells, i.e., in the nucleus of such cells, and thus chromatin may be provided in step S10 by providing whole cells or cell nuclei that contain chromatin. That is, chromatin may be provided within whole cells with intact cell membranes, i.e., intact plasma and nuclear membranes, that contain the chromatin. Such whole cells may be provided in a variety of ways, e.g., from blood drawn from a subject, from an engineered or other cell line such as the GM24385 cell line (e.g., Coriell Institute for Medical Research). In some cases, obtaining chromatin from any cell line that has been extensively characterized for whole genome amplification (WGA) and/or whole exome sequencing (WES) may provide advantages because the variant frequency information and/or other details regarding characteristics of the DNA of such cells may be available. This information may allow for a straightforward characterization of DNA features, thus confirming whether a cfDNA diagnostic evaluated using cfDNA reference material made from the cells is suitably accurate or otherwise effective. Thus, in some embodiments, it may be useful to have the DNA of the whole cells sequenced or otherwise defined so that synthetic cfDNA created using the whole cells will have known properties. In one example, cells from the GM24385 lymphoid cell line were used as a chromatin source, in part because these cells are one of the seven highly characterized genomes for the NIST's Genome in a Bottle Consortium. The GM24385 cells were obtained from Coriell Institute for Medical Research, and were suspension cultured in RPMI-1640 medium with L-glutamine (Lonza, Walkersville, Md., USA; Part No. 12-702Q) supplemented with fetal bovine serum and antibiotics at 37° C. for 10 days. After culturing, cells were harvested by centrifugation at 1000 relative centrifugal force (RCF) for 10 minutes and counted using the Scepter Automated Cell Counter (Millipore Corporation, Danvers, Mass., USA; Part No. PHCC00000).

It should be understood, however, chromatin may be provided in other ways than contained within whole cells. For example, chromatin may be provided within the nuclear membranes of cells, e.g., obtained by lysing the plasma membrane of whole cells so as to leave the nuclear membranes containing the chromatin intact. Such cell nuclei may be isolated from other cell materials and provided with chromatin contained within the nucleic membranes. In another embodiment, chromatin may be provided without being contained in any type of cellular membrane. For example, chromatin may be recovered from cells, e.g., by lysing plasma and nuclear membranes of whole cells and separating, at least in part, the chromatin from other cell portions. Techniques for lysing cell plasma membranes and/or nucleic membranes, and isolating cell nuclei or chromatin from other cell components released by lysing are known and any suitable techniques may be used with embodiments incorporating aspects of the invention. For example, cell membranes may be lysed using acoustic energy, chemical agents (such as detergents found in lysing buffers), mechanical force such as via grinding media (bead beating) or in a douncer, and so on. Cell nuclei and/or chromatin may be separated from other cell components by centrifugation or other suitable techniques such as filtration, gel filtration etc.

In step S20, the chromatin may be treated with formaldehyde to generate crosslinks between DNA and corresponding histones in the chromatin. The inventors have found that the formation of crosslinks may help stabilize chromatin by covalently crosslinking histones to corresponding DNA which helps to keep the DNA bound tightly around corresponding histone octamers. This may aid in the later generation of nucleosomes while maintaining the nucleosome structure. In embodiments where chromatin is provided uncontained in any cell membranes, the chromatin may be treated with formaldehyde, e.g., while in a suitable solution. In some embodiments where chromatin is provided within whole cells or within cell nuclei that are not within a corresponding plasma membrane, the whole cell or cell nuclei may be treated with formaldehyde to generate the DNA/histone crosslinks. In the example above in which chromatin is provided in whole cells, the harvested GM24385 cells were suspended in 20 mL of Covaris fixation buffer (truChIP Chromatin Shearing Reagent Kit; Covaris, Woburn, Mass., USA; Part No. 520154) at a concentration of $2.1 \times 10^7$ cells/mL, and then fixed with 2 mL of methanol-free formaldehyde for 10 minutes at room temperature. The formaldehyde fixing reaction was stopped by the addition 1.2 mL quenching buffer to the cell solution and incubation at room temperature for five minutes. The quenching buffer was obtained from a truChIP Chromatin Shearing Reagent Kit (Covaris, Woburn, Mass., USA; Part No. 520154). The fixed cells were subsequently washed in phosphate buffered saline (PBS) and cell pellets ($4.3 \times 10^7$ cells each) were stored at minus 80 degrees C. The cells containing fixed chromatin (i.e., chromatin with crosslinks between DNA and corresponding histones) and are stable for an extended period, such as days, weeks or months, before subsequent processing. It should also be understood that chromatin, whether provided within a cellular membrane or not, may be fixed (treated with formaldehyde) in a continuous, or semi-continuous, process. For example, chromatin may be provided into a flow path and fixed while in the flow path, e.g., chromatin may flow into a treatment chamber and fixed with formaldehyde while located in the treatment chamber. The fixed chromatin (whether contained within cell membranes or not) may flow out of the treatment chamber for further processing as discussed below, or may remain in the treatment chamber for one or more additional processes.

In step S30, the chromatin having crosslinks formed by formaldehyde treatment are exposed to acoustic energy (focused or unfocused) to shear the chromatin. If the fixed chromatin is provided separate from any cell membrane, the fixed chromatin may be suitably processed with acoustic energy as described in more detail below. However, if the fixed chromatin is provided within a cell membrane, e.g., within both a plasma membrane and a nuclear membrane, or within only a nuclear membrane, one or more cell membranes may be lysed to release the chromatin prior to shearing of the fixed chromatin. In the example above, whole cells were treated with formaldehyde to provide crosslinks between DNA and corresponding histones, and so plasma and nuclear membranes were subsequently lysed to release the fixed chromatin for shearing. In the example above, the stored frozen cells were resuspended in 3.2 mL of a lysis buffer consisting of 10 mM Tris HCl, 5 mM CaCl2, pH 8.0, and 130 µL aliquots of this suspension were respectively dispensed into snap cap microTUBEs with AFA fiber (Covaris, Woburn, Mass., USA; Part No. 520045). Cell density was $3.3 \times 10^6$ cells per 130 µL in a Covaris 130 ul microTUBE. Alternatively, $3.3 \times 10^7$ of the cells (or another suitable number) may be provided in a Covaris 1 mL milliTUBE with AFA fiber (part number 520130). The tubes holding the cell samples were exposed to focused acoustic energy using a Covaris E220 instrument with intensifier at 105 W peak incident power (PIP), 5% duty cycle (DC), and 200 cycles per burst (CPB) for 25 minutes at 4 degrees C. This acoustic energy treatment served to lyse the cell membranes, both plasma and nuclear membranes, as well as to partially shear the fixed chromatin. The processing conditions for $3.3 \times 10^7$ cells in a milliTUBE were 140 W peak incident power (PIP), 10-15% duty cycle (DC), and 200 cycles per burst (CPB) for 25-40 minutes at 4 degrees C. to both lyse cell membranes and shear the fixed chromatin. Thus, in some embodiments, the focused acoustic energy may be used to lyse both the plasma and nuclear membranes, as well as shear the formaldehyde crosslinked chromatin into smaller fragments, e.g., in the size range of 1-5 kb. If chromatin is provided within nuclear membranes only (no plasma membrane), suitable acoustic energy may be used to lyse the nuclear membrane and shear the chromatin.

Shearing of the fixed chromatin by acoustic energy may produce fragments of chromatin that include one or more nucleosomes. That is, in some cases, single nucleosomes include a 147 bp segment of DNA wrapped around a corresponding histone octamer 1.75 times, and formaldehyde treatment forms crosslinks between the DNA and corresponding histone. Linker DNA segments having a length of 20-80 bp link one nucleosome to another, but such linker segments may not have crosslinks formed with any histone by the formaldehyde treatment. The acoustic energy treatment may release DNA from the cells (by lysing cell membranes, if needed), and shear the DNA at linker segments so as to form multiple-nucleosome chromatin segments having a fragment size of about 1-5 kbp. This partial shearing of chromatin has been found to enhance or otherwise improve the effect of subsequent enzyme treatment, discussed in more detail below.

While in the example above chromatin is provided in whole cells which are lysed by focused acoustic energy which also shears the chromatin, the use of focused acoustic energy is not required. Of course, where chromatin is provided for shearing separate from any cell membrane, the acoustic energy need not lyse any cell membrane and may shear chromatin only. Also, even where fixed chromatin is provided within a cell membrane (whether a nuclear membrane only or both plasma and nuclear membranes), the cell membranes may be lysed in ways other than by focused acoustic energy. For example, as mentioned above, cell membranes may be lysed by unfocused acoustic energy (sonication), chemical agents (such as detergents), and any other suitable technique. With chromatin released from any cell membrane, the chromatin may be sheared by acoustic energy, whether focused or unfocused.

Also, although a same focused acoustic energy (e.g., having the same or similar parameters such as PIP, duty cycle, cycles per burst, etc.) is used in the example above to both lyse cell membranes and shear fixed chromatin, different acoustic energy parameters may be used to lyse cell membranes and to shear chromatin. For example, a first set of focused acoustic energy parameters may be used to lyse cell membranes to release fixed chromatin, and then a second set of focused acoustic energy parameters may be used to shear the released chromatin. As an example, different peak incident power (PIP) settings may be used to lyse membranes and to shear chromatin so that the lysing process does not shear the chromatin. This may help ensure that the chromatin is not sheared during lysing, but is sheared in a desired way using a different type of focused acoustic energy, e.g., so that desired shearing results are achieved.

As noted above, chromatin may be sheared in a flow through type process that may be continuous or semi-continuous (e.g., where portions of material in a product flow are kept in a particular processing area for a period of time and then permitted to flow to a downstream processing location). For example, whole cells that are treated with formaldehyde in a first treatment chamber may flow out of the first treatment chamber and into a second treatment chamber where cell membranes are lysed (e.g., by focused acoustic energy, unfocused acoustic energy, chemical agents, etc.). This may release fixed chromatin, which may flow to a third treatment chamber where the chromatin is sheared by focused acoustic energy. In other embodiments, fixing of the chromatin, lysing of the cell membranes and shearing of chromatin may be performed in a single treatment chamber, or in two or some other suitable number of treatment chambers (e.g., fixing and lysing may occur in a first chamber, and chromatin shearing occurs in a second chamber, or fixing occurs in a first chamber, and lysing and chromatin shearing occurs in a second chamber).

In step S40, with fixed chromatin sheared, the chromatin may be treated with an enzyme to digest chromatin in linker regions of the DNA between nucleosomes and to generate nucleosome material. This enzyme treatment produces single and/or multiple nucleosome fragments from the sheared chromatin by digesting DNA in linker regions between nucleosomes. Also, the enzyme treatment may be performed in individual sample tubes or other vessels, or in a flow through process as discussed above. In a flow through process, enzyme treatment may occur as sheared chromatin flows through a portion of a treatment system, or while the sheared chromatin is located in a particular treatment chamber (which may be used to perform one or more other process treatments such as shearing, lysing, etc.). In some embodiments including the examples above, MNase was used to generate nucleosomes, e.g., with an average fragment size of around 147-195 bp, although other suitable enzymes as listed earlier can be used. Specifically, for the examples above, micrococcal nuclease, micrococcal nuclease buffer, and purified bovine serume albumin (BSA) were obtained from New England BioLabs (Ipswich, Mass., USA; Kit Part No. M0247S). The MNase was diluted at a ratio of 1:100 in 1× micrococcal nuclease buffer supplemented with BSA (0.1 mg/mL final concentration). MNase activity of the diluted enzyme was 20 U/mL. To each 130 μL sample contained in a microTUBE, 13 μL of 10× micrococcal nuclease buffer and 10.4 μL of diluted MNase was added. The enzyme reactions were performed for 0, 5, 10, 15, or 20 minutes to assess the differing effect of the enzyme treatment over time on the samples. The reactions were stopped by the addition of 18 mM EGTA, 10 mM EDTA, and 13 μL Proteinase K (Sigma-Aldrich, St. Louis, Mo., USA; Part No. P-4850) to digest all the proteins including histones. The reactions were then incubated overnight at 65 degrees C. with rotary shaking at 600 rpm to allow for efficient Proteinase K digestion, and reverse crosslinking of the DNA. DNA/histone fragments were purified using the MinElute PCR Purification Kit from Qiagen (Hilden, Germany; Kit Part No. 28004).

Figure 2A:
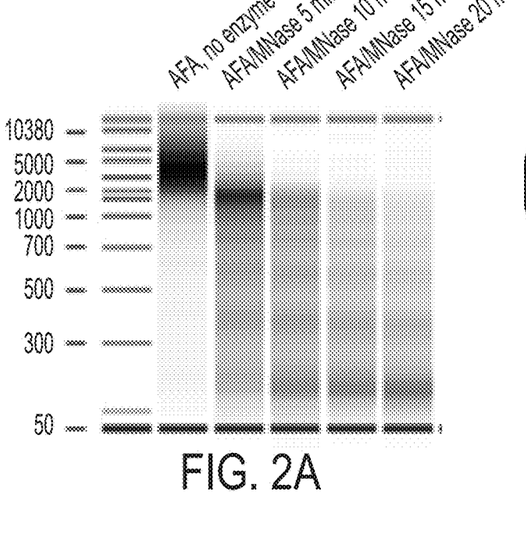
FIG. 2A shows smear results of cfDNA reference material generated using different enzyme digestion times.
Figure 2B:
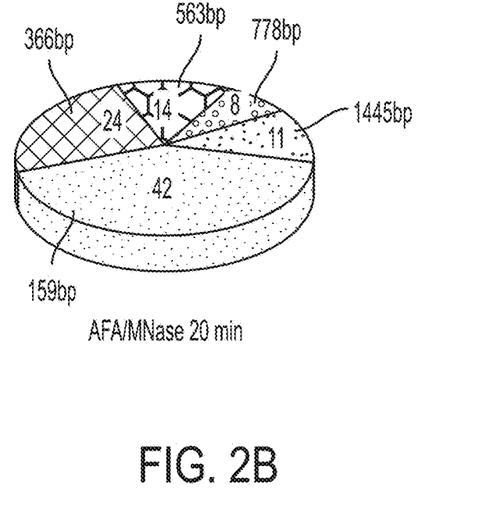
FIG. 2B shows a pie chart of fragment sizes for the experiment in FIG. 2A involving the use of focused acoustic energy and enzyme treatment for 20 minutes.

Samples created in the examples above were analyzed on an Agilent 2100 Bioanalyzer on High Sensitivity Chips (Agilent Technologies, Santa Clara, Calif., USA; Kit Part No. 5067-4626). Smear analysis was performed to determine peak size and size distribution of the nucleosome material generated as a percentage of total peak height. FIG. 2A shows the DNA fragment size distribution for fixed chromatin samples that were treated respectively with (1) focused acoustic energy (identified as AFA or Adaptive Focused Acoustics) only (i.e., shearing with focused acoustic energy only and no enzyme treatment), (2) AFA and 5 minutes enzyme treatment, (3) AFA and 10 minutes enzyme treatment, (4) AFA and 15 minutes enzyme treatment, and (5) AFA and 20 minutes enzyme treatment. As can be seen, increased enzyme treatment time resulted in generally smaller average fragment sizes, with fragment size bands centered at about 1445, 778, 563, 366, and 159 bp. These fragments indicate the presence of dinucleosome, trinucleosome, and tetranucleomes, etc. in the nucleosome material. As shown in FIG. 2B, the fragment size distribution for bands produced from the 20 minute MNase treatment time was estimated as follows: 42% at 159 bp, 24% at 366 bp, 14% at 563 bp, 8% at 778 bp, and 11% at 1445 bp.

Figure 3:
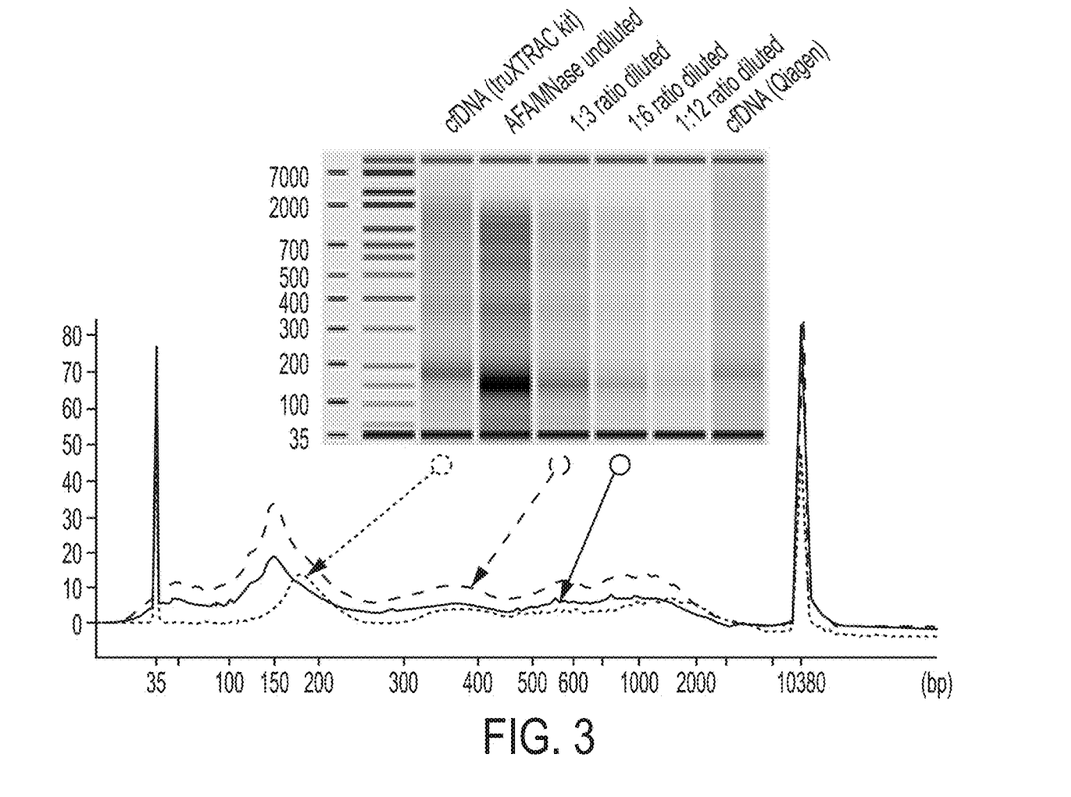
FIG. 3 shows smear results of native cfDNA and cfDNA reference material generated in an illustrative embodiment.

As can be seen in FIG. 3, cfDNA reference material produced in the examples above was compared to cfDNA material isolated from normal human plasmas with respect to fragment size distribution. Native cfDNA material was isolated from human plasmas using two different techniques, i.e., using a truXTRAC kit available from Covaris, Inc. and cfDNA obtained from Qiagen. Synthetic cfDNA reference material generated according to the examples above was used in undiluted form, and at dilution ratios of 1:3, 1:6 and 1:12. As can be seen in the smear and fragment size graph, the cfDNA reference material has a very similar fragment size distribution to that of native, isolated cfDNA.

In some embodiments, cell membranes may be lysed and/or shearing of chromatin may be performed by focused acoustic energy while the cells are located in a buffer solution that is compatible with enzyme treatment, such as use of MNase, to digest portions of the DNA. As a result, cells and/or chromatin released during lysing need not be removed from a buffer solution used for lysing prior to subsequent shearing and/or enzyme treatment. Instead, enzyme treatment may be performed in the same solution used for lysing and/or shearing. This arrangement may provide not only increase yield of cfDNA reference material (e.g., because no material is lost due to separating DNA from a buffer solution), but also provide for scalability in the cfDNA generation process. For example, larger batches of cells and cell material may be processed using acoustic energy and treated with enzyme because there is no need to separate released chromatin from a solution used for lysing or shearing. In some cases, acoustic energy and enzyme treatment may be performed in a flow through system where whole cells are continuously flowed into a treatment chamber where cells are lysed by focused acoustic energy, released chromatin is sheared by focused acoustic energy, and sheared chromatin is enzyme digested to form desired nucleosome material. Thus, synthetic cfDNA material may be continuously produced without the need for individual sample tubes or other holders. Also, aspects of the invention allow for more highly diluted enzyme for linker digestion, e.g., because focused acoustic energy may be used to enhance the activity of MNase or other suitable enzyme either directly by facilitating enzyme activity or indirectly by partially shearing DNA chromatin prior to enzyme digestion.

In another embodiment, crosslinked DNA may be treated with limiting concentrations of endonuclease or a cocktail of different endonuclease. The released DNA fragments may then be separated from the nucleosomal fraction by centrifugation, gel filtration, density gradients or other methods. Separation may be proceeded by focused acoustic energy treatment to dissociate free DNA from the nucleosomal conglomerate. This fraction can be combined with the DNA isolated from the nucleosomal fraction (as described in detail above) to provide a cfDNA-like material that includes DNA from nucleosomal as well as heterochromatinal origin.

In accordance with another aspect of the invention, DNA material generated using the methods described above may be used as a cfDNA reference material alone, or the DNA may be combined with other DNA fragments or other material. For example, the nucleosome material generated by enzyme treatment may be combined with other DNA fragments, e.g., to provide the combined nucleosome material and DNA fragments with an average fragment size of 165 to 180 bp (native cfDNA typically has a fragment size in this range). In other embodiments, the nucleosome material may be combined with DNA fragments having known mutations to create a cfDNA reference material. For example, since the genome of the GM24385 cell line is very well characterized, the publically available DNA sequence can be used to design double stranded oligonucleotide cassettes of varying sizes to partially cover, or fully cover a whole gene or part of the gene containing the desired mutation, for specific genes with specific mutations in the exon, intron, promotor regions, etc. In addition, or alternately, a similar approach can be used to introduce insertion and deletion mutations. As an example, a random, or non-random pool of 150-200 mer double stranded oligonucleotides for the BRAF gene can be designed with each of the oligonucleotides containing the clinically actionable V600E mutation. By titrating this pool against the synthetic cfDNA reference material formed as discussed above, a wide range of variant allelic frequencies for that mutation can be introduced into the composite cfDNA reference material. A similar approach can be used to introduce any desired mutation, or a combination of any number of mutations into the synthetic cfDNA reference material.

Figure 4:
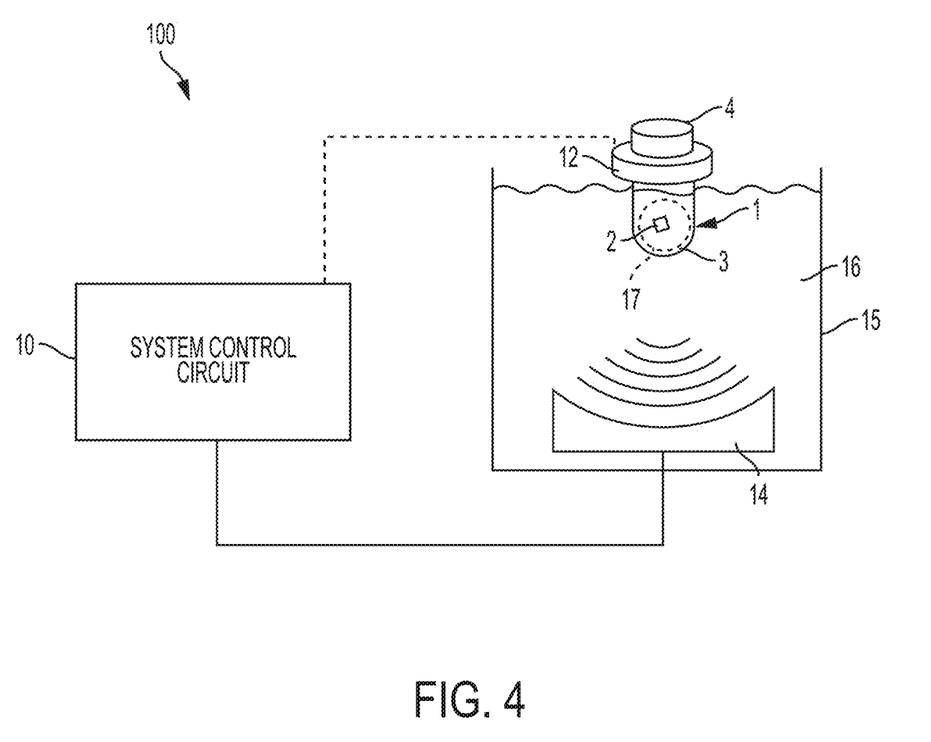
FIG. 4 shows a schematic block diagram of an acoustic treatment system that incorporates one or more aspects of the invention.

FIG. 4 shows a schematic block diagram of an acoustic treatment system 100 that incorporates one or more aspects of the invention and/or can be employed with one or more aspects of the invention. It should be understood that although embodiments described herein may include most or all aspects of the invention, aspects of the invention may be used alone or in any suitable combination with other aspects of the invention. In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 4. The sample 1 may include "solid" particles, such as cells, or other material 2, such as cell-free DNA or other nucleic acid material, and/or liquid 3, such as blood serum, water, other solution, etc. Under the control of a control circuit 10 (described in more detail below), the acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control. The focal zone may be stationary relative to the sample, or it may move relative to the sample.

In some embodiments, the transducer can be formed of a piezoelectric material, such as a piezoelectric ceramic. The ceramic may be fabricated as a "dome", which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone 17 of one of these domes is typically cigar-shaped. At 1 MHz, the focal zone 17 is about 6 cm long and about 2 cm wide for a 20 cm dome, or about 15 mm long and about 3 mm wide for a 10 cm dome. The peak positive pressure obtained from such systems at the focal zone 17 is about 1 MPa (mega Pascal) to about 10 MPa pressure, or about 150 PSI (pounds per square inch) to about 1500 PSI, depending on the driving voltage. The focal zone 17, defined as having an acoustic intensity within about 6 dB of the peak acoustic intensity, is formed around the geometric focal point. It is also possible to generate a line-shaped focal zone, e.g., that spans the width of a multi-well plate and enables the system 1 to treat multiple wells simultaneously.

To control an acoustic transducer 14, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The vessel 4 may have any suitable size or other arrangement, e.g., may be a glass or metal tube, a plastic container, a well in a microtiter plate, a vial, or other, and may be supported at a location by a vessel holder 12. For example, the vessel 4 may be a cylindrical tube with a flat bottom and a threaded top end to receive a cap, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes. Although a vessel holder 12 is not necessarily required, the vessel holder 12 may interface with the control circuit 10 so that the vessel 4 and the sample in the vessel is positioned in a known location relative to an acoustic field, for example, at least partially within a focal zone of acoustic energy.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

The invention claimed is:

1. A method for generating cfDNA reference material, comprising:
   providing chromatin including DNA wrapped around corresponding histones to form nucleosomes;
   treating the chromatin with formaldehyde to generate fixed chromatin including crosslinks between the DNA and corresponding histones;
   exposing the fixed chromatin to acoustic energy to shear the fixed chromatin into sheared, fixed chromatin fragments each having a size of 1 kbp to 5 kbp;
   treating the sheared, fixed chromatin fragments with an enzyme to digest chromatin in linker regions of the DNA between nucleosomes and generate nucleosome material having a size of 147 to 195 bp;
   recovering the nucleosome material having the size of 147 to 195 bp as synthetic cfDNA reference material having properties which mimic naturally occurring cfDNA; and
   providing the nucleosome material as synthetic cfDNA reference material to verify an accuracy of a diagnostic test for naturally occurring cfDNA.

2. The method of claim 1, wherein the enzyme is micrococcal endonuclease.

3. The method of claim 1, wherein the step of providing chromatin includes providing whole cells with intact cell membranes that contain the chromatin.

4. The method of claim 3, wherein the step of treating the chromatin includes treating the whole cells with formaldehyde to generate the fixed chromatin.

5. The method of claim 3, further comprising exposing the whole cells to focused acoustic energy to lyse the cells.

6. The method of claim 5, wherein the step of exposing the whole cells includes lysing both plasma membranes and nuclear membranes of the whole cells.

7. The method of claim 6, wherein the step of treating the chromatin occurs after plasma membranes and nuclear membranes are lysed.

8. The method of claim 5, wherein the step of exposing the whole cells includes lysing plasma membranes of the whole cells, and wherein the step of treating the chromatin includes treating the chromatin with formaldehyde while the chromatin is contained in a corresponding nuclear membrane.

9. The method of claim 3, wherein the whole cells are cells from the GM24385 cell line.

10. The method of claim 1, wherein the step of exposing the fixed chromatin includes exposing whole cells that contain the fixed chromatin to focused acoustic energy to lyse plasma membranes and nuclear membranes of the whole cells.

11. The method of claim 10, wherein the steps of exposing the fixed chromatin and exposing the whole cells are performed with the fixed chromatin and whole cells in a same buffer solution.

12. The method of claim 1, wherein the step of exposing the fixed chromatin includes using focused acoustic energy to shear the fixed chromatin into fragments.

13. The method of claim 1, wherein the step of treating the sheared, fixed chromatin with an enzyme includes enzymatically digesting the linker regions of the DNA to form single nucleosomes.

14. The method of claim 1, further comprising combining the nucleosome material generated through the step of treating the sheared, fixed chromatin with an enzyme with DNA fragments to provide the combined nucleosome material and DNA fragments with an average fragment size of 165 to 180 bp.

15. The method of claim 1, further comprising combining the recovered nucleosome material with DNA fragments having known mutations to create a cfDNA reference material.

16. The method of claim 1, wherein the step of exposing the fixed chromatin includes providing the fixed chromatin in a vessel and positioning at least a portion of the vessel in a fluid coupling medium that transmits focused acoustic energy to the vessel.

17. The method of claim 1, wherein the step of exposing the fixed chromatin includes arranging focused acoustic energy to have a duty cycle of 10% or less, and a peak incident power (PIP) of 20 W to 200 W.

18. The method of claim 1, wherein the step of exposing the fixed chromatin includes providing the fixed chromatin in a solution that has a volume of 10 microliters to 150 microliters.

19. The method of claim 1, wherein the steps of treating the chromatin, exposing the fixed chromatin, and treating the sheared, fixed chromatin are performed in a flow-through system including a treatment chamber in which chromatin is treated with formaldehyde, sheared by focused acoustic energy, and treated with the enzyme, and the nucleosome material flows out of the treatment chamber.

20. The method of claim 1, wherein the acoustic energy is focused acoustic energy having a frequency between 100 kilohertz and 100 megahertz and a focal zone to which the fixed chromatin is exposed.

* * * * *